US00PP12043P2

(12) United States Plant Patent

Lim et al.

(10) Patent No.: US PP12,043 P2

(45) Date of Patent: Aug. 7, 2001

(54) PEACH TREE 'MOON LIGHT'

(76) Inventors: Jung-Kyoung Lim; Sung-Hun Lim, both of 637-1 Whoulhari, Seomyun, Yunkikun, Chungnam (KR)

( * ) Notice: Subject to any disclaimer, the term of this patent is extended or adjusted under 35 U.S.C. 154(b) by 0 days.

(21) Appl. No.: 09/217,601

(22) Filed: Dec. 21, 1998

(51) Int. Cl.[7] ..... A01H 5/00

(52) U.S. Cl. ..... Plt./195

(58) Field of Search ..... Plt./195

*Primary Examiner*—Bruce R. Campell
*Assistant Examiner*—Melissa L. Kimball

(74) *Attorney, Agent, or Firm*—Gilberto M. Villacorta; Pepper Hamilton LLP; Paul D. Roath

(57) ABSTRACT

A new and distinct variety of peach *'Prunus persica'* tree with the following combination of unique features that are desirable in a new variety.

1. Heavy and rugular production of fruit.
2. Production of very firm, white flesh fruit with good handling and shipping quality.
3. Fruit that will stay firm on the tree 15 to 17 days after maturity (shipping ripe).
4. Fruit with excellent flavor and eating quality.
5. Early season maturity of white flesh fruit.
6. Fruit with an attractive red skin.
7. Vigorous half-open growth.

3 Drawing Sheets

BACKGROUND OF VARIETY

In the country of origin, Republic of Korea, the tree of this disclosure is believed to have been derived from the Korean commercial variety 'Yumyeong' (unpatented), which has been selected among the crosses of 'Yamato-wase'×'Nunome-wase' in Korea and within the subspecies 'dianthiflora' (Dipp.); and originated on the hillock in Seomyun, Yunkikun, Chungnam, Republic of Korea. The appropriate botanical classification for this tree is believed to be *'Prunus persica'*. This subject tree is believed to be exceptional in a number of characteristics and will offer a further option to commercial growers of stone fruits in terms of fruit having large to very large size, firm flesh, clingstone, sweet, attractively colored fruit which has a comparatively high capacity to withstand handling, shipping and storage. Having the additional desirable fruit characteristics of heavy production of fruit with an attractive round shape and pleasant, sweet taste, and which is harvested earlier than normal harvest for fruit of extra large size, this tree promises to be a valuable new variety to industry and commerce which has value as a dessert variety but which may also be used as a canner. This tree further has the advantage of being mid to late-season in blooming so that it is less susceptible to late frosts than other locally adapted tree varieties. We are not aware of varieties, which offer a similar or comparable combination of characteristics.

ORIGIN OF THE VARIETY

The new tree was selected from among several thousand seedlings from 'Yumyeong' variety, which had been planted on our farm on the hillock in Seomyun, Yunkikun, Chungnam, Korea. The seedling was discovered near a specimen of the noted apparent seed parent. The parent tree, 'Yumyeong', is a late season variety that normally ripens between August 21 and September 10, which is 125 days from the blooming days. Our attention was drawn to this tree when we noticed that the fruit was much sweeter by about 2 to 3° (Bx) than the fruit of the parent 'Yumyeong' variety on the wood. Furthermore, the saccharinity was not changed in the rainy season on the wood, differing from other varieties including the parent 'Yumyeong' variety. Based on these observations, we selected the variety for asexual reproduction and commercialization.

ASEXUAL REPRODUCTION OF THE VARIETY

Asexual reproduction of the new and distinct variety was performed by budding in our orchard located in Seomyun, Yunkikun, Chungnam, Korea and shows that all characteristics run true to the original tree and are established and transmitted through succeeding propagation.

SUMMARY OF THE VARIETY

The present new and distinct variety of peach tree has been denominated 'Moon Light', and the height of the fully grown tree is about 3 to 3.5 meters, which is almost same with that of the tree, 'Yumyeong'. The diameter of the new tree is about 6 to 7 meters. This tree grows vigorously on standard peach rootstock with a half open shape and is a regular and productive bearer of extra large, red skin, white flesh, clingstone fruit with a mild, sweet subacidic flavor with excellent eating and stock quality. The fruit is further characterized by having very firm flesh, the ability to hang on the tree 15 to 17 days after maturity (shipping ripe), having good handling and shipping quality, a red skin and ripening in the early maturity season approximately 30 days before 'Yumyeong' and appoximately 10 days after 'Wangdo' (U.S. Plant Pat. No. 10,833) which are established commercial varieties in Korea. The color and size of the fruit, the size and shape of the tree and self pollinating are very similar to 'Wangdo'.

DESCRIPTION OF THE PHOTOGRAPHS

Figure 1:
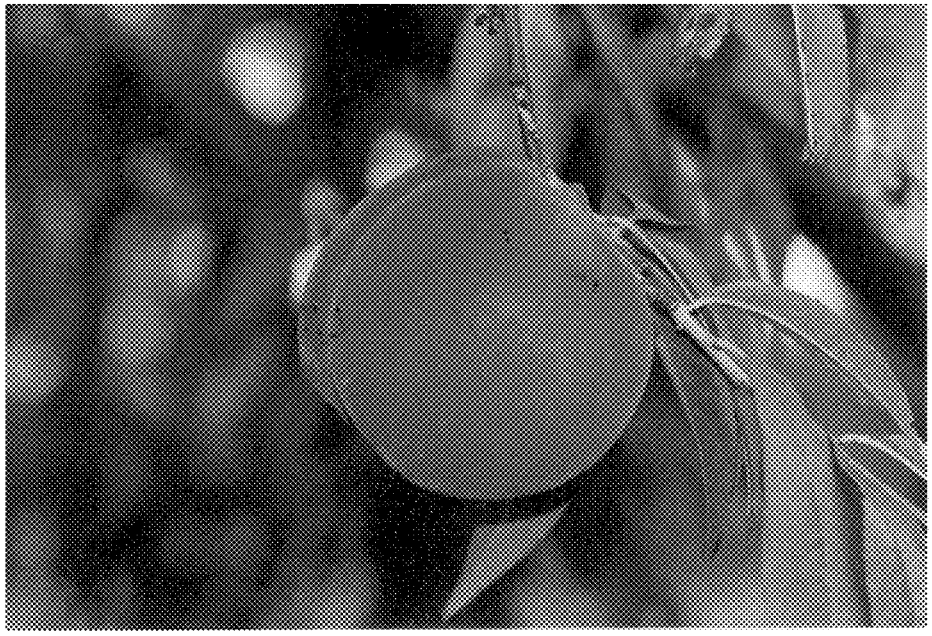
FIG. 1 shows typical specimens of the fruit of the new and distinct peach variety; and typical leaf from the tree, 'Moon Light'. The illustrations show a side view of the fruit with leaves attached to the tree.
Figure 2:
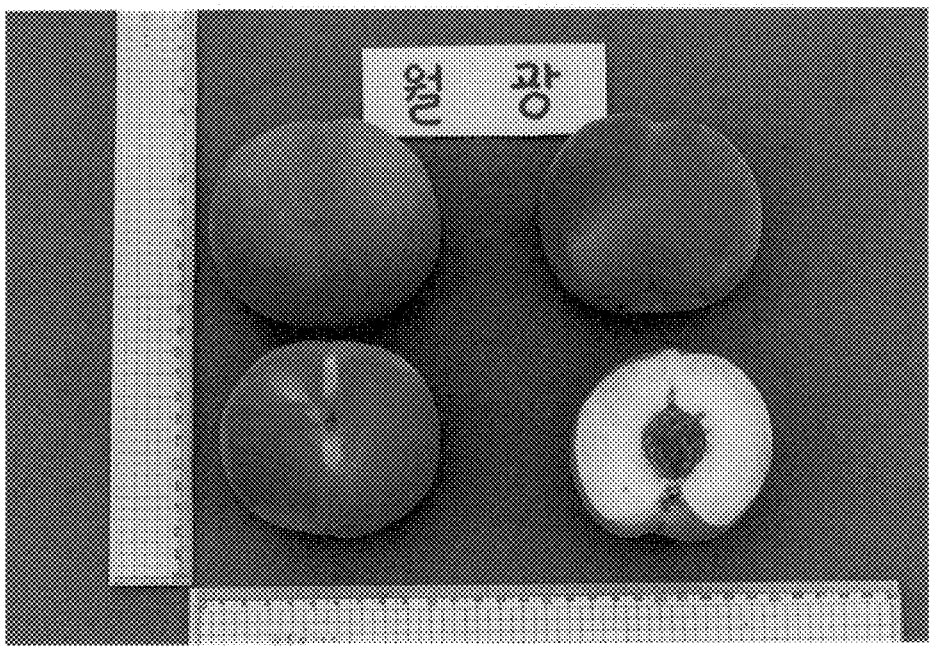
FIG. 2 shows a bottom view, front view, plane view, and a fruit divided in its suture plane to reveal flesh coloration, clock-wisely.
Figure 3:
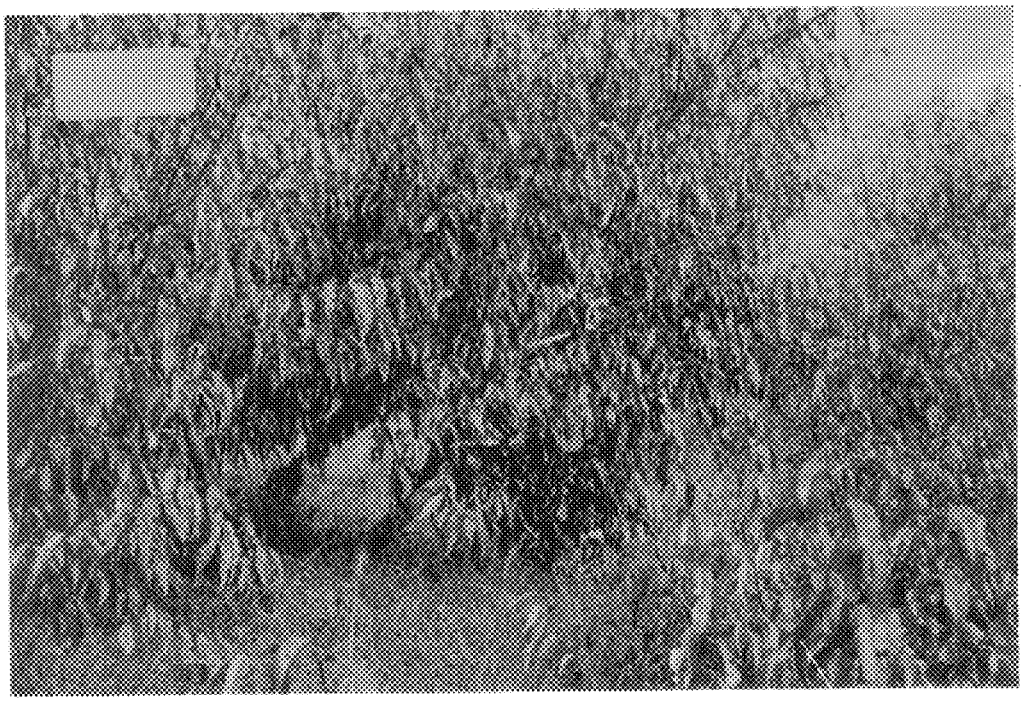
Figure 4:
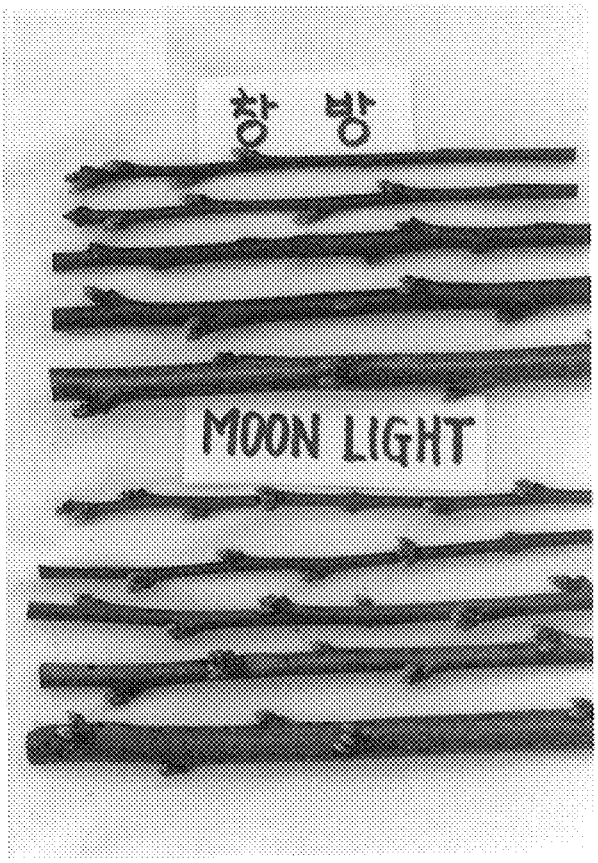

FIG. 3 shows a peach tree 'Moon Light'. This photographic illustration was taken after almost leaves was fallen; and FIG. 4 depicts the comparative picture of sprouts between the parent tree 'Yumyeong' and the present tree 'Moon Light'. (The ripening season of present 'Moon Light' is approximately same with that of 'Yumyeong' variety, and therefore we selected 'Yumyeong' variety as a comparative one.)

Figure 5:
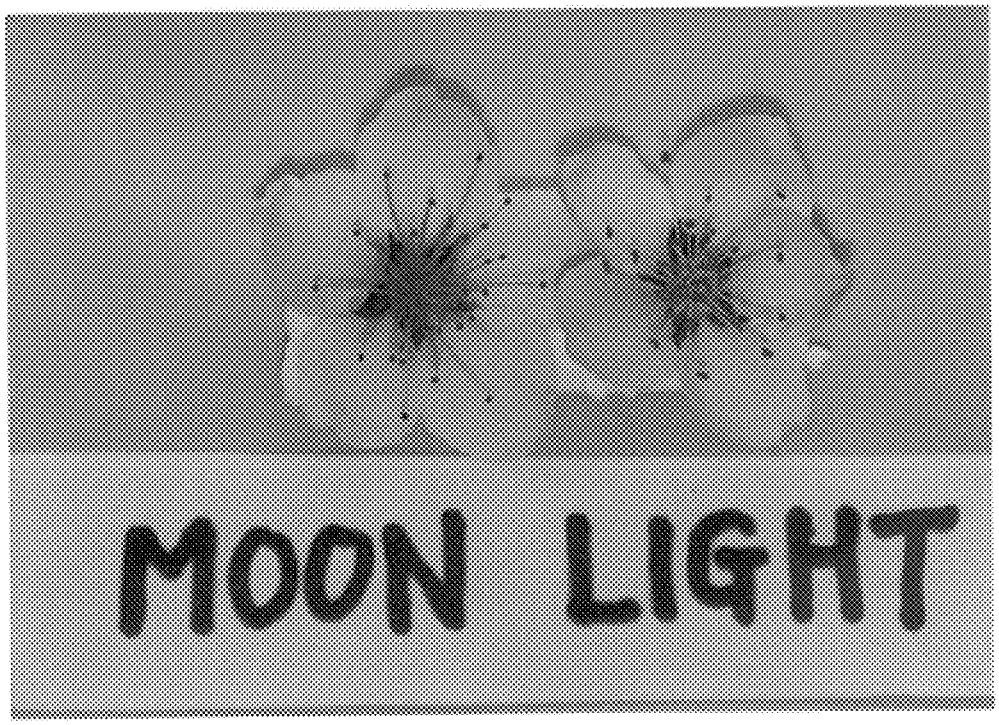

FIG. 5 shows typical flowers of the new and distinct tree 'Moon Light'.

The colors in the photographs are as nearly true as is reasonably possible in a color representation of this type;

DESCRIPTION OF THE VARIETY

The following is a detailed botanical description of the new and distinct variety of peach tree, its flowers, fruit and foliage as based on observations of the specimen grown in my orchard located on the hillock in Seomyun, Yunkikun, Chungnam, Korea, with color terminology (except those in common terms) in accordance with PANTON® Professional Color System Selector (Pantone, Inc., 1984, 1990).

Tree:

*Size.*—Large.

*Vigor.*—Vigorous. Having terminal growth of 1.5 to 2 meters per year, with the growth of the trunk terminating at the height of 3 to 3.5 meters in 3 or 4 years, in Chungnam, Korea.

*Form.*—Usually pruned to half open shape. The new peach tree grows 1.5 to 2 meters every year from the first to the third year, with the trunk terminating at about 3 meters height and then the trunk thickening every year, and the branches extending upwardly at an angle of 40 to 55°, growing 1.5 meters to 2 meters a year to a maximum extent of 6 to 7 meters. Almost the same branching with the parent tree 'Yumyeong'. To obtain large fruit, about 80% pruning of the flowers are necessary.

*Production.*—Productive (about 3000 kg/10a).

*Bearing.*—Regular.

*Density.*—Medium dense.

Trunk:

*Size.*—Medium to stocky.

*Texture.*—Smooth.

*Color.*—Brown (18-1124) to (18-1222).

Branches:

*Size.*—Medium.

*Texture.*—Varies from smooth to medium rough with maturity.

*Lenticels.*—Medium size. Medium number.

*Color.*—Brown (18-1031) to (18-1130) having small parts with light green (16-6329) to (16-6339).

Leaves:

*Size.*—Medium to large. The shape and size are almost the same as those of 'Yumyeong' variety.

*Average length.*—17 to 18.8 cm.

*Average width.*—3.5 to 4.0 cm.

*Form.*—Lanceolate-pointed.

*Texture.*—Smooth.

*Thickness.*—Medium.

*Margin.*—Crenate.

*Petiole.*—Medium length. Medium thickness.

*Glands.*—Reniform. Number varies from 0 to 5. Average number 2. Located on base of leaf blade and upper portion of petiole.

*Color.*—Upper surface green to dark green (18-01117) to (18-0322). Lower surface dull green to grayish green (17-6319) to (17-0119).

Flower buds:

*Size.*—Medium.

*Form.*—Plump.

*Length.*—Medium.

*Pubescence.*—Pubescent.

Flowers:

*Size.*—Medium — non-showy.

*Blooming period.*—April 15 to 20, 1998, which has the same flowering with 'Yumyeong' peach tree. The tree is self-fertile and so it does not require artificial fertilization.

*Color.*—Starts with white and changes to red.

*Pollen.*—Abundant. Number of Petals.

Fruit:

*Maturity when described.*—Firm ripe.

*Date of first picking.*—Aug. 15, 1998.

*Date of last picking.*—Aug. 25, 1998.

*Size.*—Extra large. Average diameter axially 8.5 to 12.5 cm. Average transversely in suture plane 8.0 to 11.5 cm.

*Form.*—Globose — slightly tip at apex and slightly flattened on stem end. The fruit is exceptionally symmetrical.

*Suture.*—Shallow but pronounced, extends from base to apex.

*Ventral surface.*—Nearly rounded, very slightly lipped.

*Apex.*—Varies from rounded to slight pistil point.

*Base.*—Retuse.

*Cavity.*—Rounded to slightly elongated in suture plane. Average depth — 1.5 cm. Average breadth 2.0 cm.

*Acidity.*—Slight.

*Saccharinity.*—12–13° Bx.

Skin:

*Thickness.*—Medium.

*Texture.*—Tenacious to flesh.

*Tendency to crack.*—None.

*Down.*—Moderate amount, short to very short in length.

*Color.*—Red (17-2036) to (18-1660).

Flesh:

*Texture.*—Very firm.

*Ripens.*—Evenly.

*Fibers.*—Small, tender.

*Juice.*—Moderate.

*Flavor.*—Excellent, mild, acidic sweet.

*Aroma.*—Moderate.

*Eating quality.*—Excellent.

*Amygdalin.*—Undetected.

*Color.*—White (no Pantone number).

Stone:

*Type.*—Clingstone.

*Size.*—Large. Average length 2.7 cm. Average width 2.6 cm. Average thickness 1.7 cm.

*Form.*—Ovoid.

*Base.*—Mostly straight — some rounded.

*Apex.*—Acuminate.

*Sides.*—Equal.

*Surface.*—Irregularly furrowed toward apex, ridges usually rounded, pitted toward base.

*Tendency to split.*—None.

*Color.*—Brown to reddish brown (18-1540) to (19-1540).

Use: The fruit of the present new variety is well suited for novelty, processing and canning, as well as for use as a dessert peach.

*Market.*—Local and long distance.

Keeping quality: Very good.

Shipping quality: Very good.

The new and distinct variety of peach tree, its foliage and fruit described above may vary in slight detail due to variations in climate, soil conditions and cultural practices under which the variety may be grown. The botanical description above is that of the variety grown under the ecological conditions prevailing near Seomyun, Yunkikun, Chungnam, Korea.

We claim:

1. A new and distinct variety of peach tree, substantially as illustrated and described, characterized in that the tree is large, grows vigorously with a half open shape and is a regular and productive bearer of large, early season maturing, white flesh, clingstone fruit with excellent flavor and eating quality; the fruit is further characterized in that it has vey firm flesh, good handling and shipping quality and has a skin with pink overspread with light yellow.

* * * * *